US011896822B2

(12) United States Patent
Tepic et al.

(10) Patent No.: US 11,896,822 B2
(45) Date of Patent: Feb. 13, 2024

(54) GAIT-CORRECTING SYSTEMS TO PREVENT DEGENERATIVE DISEASE OF JOINTS AND LIGAMENTS IN DOGS

(71) Applicant: Kyon AG, Zürich (CH)

(72) Inventors: Slobodan Tepic, Zürich (CH); Stephen Bresina, Davos (CH)

(73) Assignee: Kyon AG, Zurich (CH)

( * ) Notice: Subject to any disclaimer, the term of this patent is extended or adjusted under 35 U.S.C. 154(b) by 148 days.

(21) Appl. No.: 16/967,812

(22) PCT Filed: Mar. 11, 2019

(86) PCT No.: PCT/EP2019/056045
§ 371 (c)(1),
(2) Date: Aug. 6, 2020

(87) PCT Pub. No.: WO2019/175115
PCT Pub. Date: Sep. 19, 2019

(65) Prior Publication Data
US 2021/0038886 A1   Feb. 11, 2021

(30) Foreign Application Priority Data

Mar. 13, 2018   (EP) .................................. 18161528

(51) Int. Cl.
*A61N 1/36*   (2006.01)
*A61B 5/11*   (2006.01)
(Continued)

(52) U.S. Cl.
CPC .......... *A61N 1/36003* (2013.01); *A61B 5/112* (2013.01); *A61N 1/08* (2013.01);
(Continued)

(58) Field of Classification Search
None
See application file for complete search history.

(56) References Cited

U.S. PATENT DOCUMENTS 4,677,973 A    7/1987  Slocum
5,476,441 A *  12/1995 Durfee .................. A61F 5/0102
                                                       623/44
(Continued)

FOREIGN PATENT DOCUMENTS

EP        3154627 A1    4/2017
JP     2008-264114 A   11/2008
(Continued)

OTHER PUBLICATIONS

Arnoczky and Marshall, "The cruciate ligaments of the canine stifle: an anatomical and functional analysis", Am. J. Vet. Res. vol. 38, No. 11, 1977, pp. 1807-1814.
(Continued)

*Primary Examiner* — Shirley X Jian
(74) *Attorney, Agent, or Firm* — Rothwell, Figg, Ernst & Manbeck, P.C.

(57) ABSTRACT

The present invention relates to devices and methods useful in training dogs how to control the muscles involved in rotation of the tibia in order to reduce the risk of cranial cruciate rupture. The invention has further applications in training dogs to increase abduction of the hind limbs to avoid hip dysplasia, as well as abduction of the front limbs to avoid elbow dysplasia.

9 Claims, 3 Drawing Sheets

US 11,896,822 B2
Page 2

(51) Int. Cl.
*A61N 1/08* (2006.01)
*G16H 40/67* (2018.01)
*A61B 5/00* (2006.01)

(52) U.S. Cl.
CPC .......... *A61B 5/0024* (2013.01); *A61B 5/6828* (2013.01); *A61B 2503/40* (2013.01); *A61N 1/3603* (2017.08); *G16H 40/67* (2018.01)

(56) References Cited

U.S. PATENT DOCUMENTS

| | | | |
|---|---|---|---|
| 5,643,332 A * | 7/1997 | Stein | A61N 1/36003 607/149 |
| 9,974,478 B1 * | 5/2018 | Brokaw | A61B 5/486 |
| 10,086,196 B2 * | 10/2018 | Glukhovsky | A61B 5/4836 |
| 10,390,755 B2 * | 8/2019 | Goodall | A61N 1/36021 |
| 10,773,079 B2 * | 9/2020 | Keller | A61N 1/36031 |
| 10,792,139 B2 | 10/2020 | Tepic | |
| 11,571,146 B2 * | 2/2023 | Schroeck | A61B 5/6831 |
| 2004/0167420 A1 * | 8/2004 | Song | A61B 5/053 600/595 |
| 2011/0137375 A1 * | 6/2011 | McBride | A61B 5/1124 607/48 |
| 2011/0208444 A1 * | 8/2011 | Solinsky | A61B 5/1114 702/41 |
| 2012/0059432 A1 * | 3/2012 | Emborg | A61N 1/36034 607/49 |
| 2012/0253234 A1 * | 10/2012 | Yang | A61B 5/1038 600/595 |
| 2013/0253299 A1 * | 9/2013 | Weber | A61B 5/4064 607/45 |
| 2015/0100104 A1 * | 4/2015 | Kiani | A61N 1/36003 607/49 |
| 2016/0198995 A1 * | 7/2016 | Yeung | A61B 5/1118 600/595 |
| 2017/0042467 A1 * | 2/2017 | Herr | A61B 5/112 |
| 2017/0106189 A1 * | 4/2017 | Keller | A61N 1/0484 |
| 2017/0156662 A1 * | 6/2017 | Goodall | A61B 5/7282 |
| 2017/0164876 A1 * | 6/2017 | Hyde | A61B 5/1118 |
| 2017/0202724 A1 * | 7/2017 | De Rossi | A61H 3/00 |
| 2018/0307314 A1 * | 10/2018 | Connor | A61B 5/1123 |
| 2020/0008715 A1 * | 1/2020 | Schroeck | A61B 5/6831 |
| 2020/0008745 A1 * | 1/2020 | Burch, V | G16H 50/30 |
| 2020/0147384 A1 * | 5/2020 | Caban | A61N 1/36139 |
| 2021/0038886 A1 * | 2/2021 | Tepic | A61B 5/112 |

FOREIGN PATENT DOCUMENTS

| | | |
|---|---|---|
| JP | 2011-530356 A | 12/2011 |
| JP | 2014-533183 A | 12/2014 |
| JP | 2017-515515 A | 6/2017 |
| WO | 2010017769 A1 | 2/2010 |
| WO | 2013071307 A1 | 5/2013 |
| WO | 2015148184 A1 | 10/2015 |
| WO | 2015/188889 A1 | 12/2015 |

OTHER PUBLICATIONS

Boudrieau, "Tibial plateau leveling osteotomy or tibial tuberosity advancement?", Vet Surg., 38, 2009, 22 pages.
Dogs in Motion, M.S. Fischer and K.E. Lilje, 2nd edition 2014, VDH Service GmbH, Dortmund, p. 128.
Miller's Anatomy of the Dog, Third Edition, W.B. Saunders Company, 1993, p. 373.
Slocum and Devine, "Cranial tibial wedge osteotomy: A technique for eliminating cranial tibial thrust in cranial cruciate ligament repair", J. Am. Vet. Med. Assoc., vol. 184, No. 5, 1984, pp. 564-569.
Slocum and Slocum, "Tibial plateau leveling osteotomy for repair of cranial cruciate ligament rupture in the canine", Vet. Clin. North Am., vol. 23, No. 4, 1993, pp. 777-795.
Sumner et al., "Caudal cruciate ligament damage in dogs with cranial cruciate ligament rupture", Veterinary Surgery, 39, 2010, pp. 936-941.
Tepic et al., "Biomechanics of the stifle joint", in Proceedings of the 1st World Orthopaedic Veterinary Congress, Munich, Germany, 2002, pp. 189-190.
Notification of Transmittal of The International Search Report and The Written Opinion of the International Searching Authority cited in PCT/EP2019/056045 dated May 15, 2019, 14 pages.
Japanese Notification of Reasons for Rejection issued in Patent Application No. 2020-548632 dated Dec. 14, 2022, 22 pages.

* cited by examiner

GAIT-CORRECTING SYSTEMS TO PREVENT DEGENERATIVE DISEASE OF JOINTS AND LIGAMENTS IN DOGS

CROSS REFERENCE TO RELATED APPLICATION

This application is a 35 U.S.C. 371 National Phase Entry Application from PCT/EP2019/056045, filed Mar. 11, 2019, which claims the benefit of European Patent Application No. 18161528.7 filed on Mar. 13, 2018, the disclosure of which is incorporated herein in its entirety by reference.

FIELD OF THE INVENTION

The present invention relates to devices and methods useful in training dogs how to control the muscles involved in rotation of the tibia in order to reduce the risk of cranial cruciate rupture. The invention has further applications in training dogs to increase abduction of the hind limbs to avoid hip dysplasia, as well as abduction of the front limbs to avoid elbow dysplasia.

BACKGROUND OF THE INVENTION

The anterior cruciate ligament (ACL) in the human knee joint, commonly called the cranial cruciate ligament (CrCL) in the canine stifle, is frequently torn in trauma. In dogs, in most cases, CrCL fails after a degenerative process of a still not fully understood etiology.

In human orthopedics, standard procedures replace the failed ACL with an ACL allograft or a surrogate autograft made from a part of the patient's own patellar tendon or a part of the fascia and tendon removed from the hamstring muscles. The procedure results in a stable knee, but the long-term performance of the knee is often unsatisfactory. Roughly 75-90% of cases result in degenerative arthritis of the joint within 15 years of the procedure.

In dogs, the standard procedure involves either placement of an extra-capsular suture or performing one of several geometry-modifying surgical techniques. In the extra-capsular procedure, a suture is placed outside of the joint, usually on the lateral side, to approximate the function of the CrCL. The intention of the suture application is to provide stability of the joint for several weeks while waiting for fibrosis to occur around the joint. This fibrosis should then provide for long-term stability. However, the extra-capsular suture technique regularly results in failure. Degenerative arthritis of the joint, after a year or so, is the rule rather than an exception.

Attempts to replace the CrCL in the dog by an anatomically placed, intra-articular artificial ligament have also generally failed in spite of years of research and development of materials, anchor designs, and surgical techniques.

In surgical, geometry-modifying techniques, the tibia is cut and a segment of it is repositioned to change the geometry of the tibia and/or the joint in order to stabilize the stifle. Various techniques have been used, including: tibial plateau leveling osteotomy (TPLO; see U.S. Pat. No. 4,677, 973 and Slocum and Slocum, *Vet. Clin. North Am.* 23:777-795, 1993), cranial closing wedge osteotomy (CWO; Slocum and Devine, *J. Am. Vet. Med. Assoc.* 184:564-569, 1984), and tibial tuberosity advancement (TTA; Tepic et al., *Biomechanics Of The Stifle Joint*, in Proceedings of the 1st World Orthopaedic Veterinary Congress, Munich, Germany, pp. 189-190. 2002). Of the surgical approaches used in dogs, TTA seems to be associated with less morbidity and faster recovery, and it also provides immediate and durable stability to the joint (Boudrieau, *Vet Surg.*, 38(1):1-22, 2009). Nevertheless, surgical complications are not uncommon with all these techniques. The most common is post-surgical damage to the medial meniscus caused by excessive, supraphysiological movement between the femur and the tibia.

SUMMARY OF THE INVENTION

The present invention provides devices and methods useful in training dogs to control the muscles involved in rotation of the tibia in order to reduce the risk of cranial cruciate rupture. The motivation for this invention emerged from our study of the probable origin of cruciate disease in the dog and our efforts to rectify the problem of external loading that induces torque in the stifle and consequently very high tensile forces in the cruciate ligaments as they wrap around each other to limit internal rotation of the tibia, particularly at the very beginning of the stance phase.

Surgical treatment by transection of the tendon of the popliteal muscle has been proposed in the US patent application by Tepic (application Ser. No. 15/690,611) in order to eliminate intoeing of the paw as it lands on the ground. Our in vitro observations suggested that neutralizing the torque due to intoeing could reduce by several fold tensile forces in the cranial cruciate ligament or its replacement, as well as in its surrogate, a lateral suture placed extra-capsularly.

The present invention features devices and methods for preventive, non-surgical treatment of the dogs at risk for cruciate rupture, aiming at reducing the internal rotation of the tibia, by modifying the balance of the external and internal rotators of the tibia. In particular, the muscles targeted for intervention by training are the caudal portion of the biceps femoris, which is the only external rotator, acting against the internal rotators group of: sartorius, gracilis, semitendinosus, semimembranosus, and popliteus. All of these muscles, with exception of the popliteus, are also flexors of the stifle and in that function, have to balance the extensors, comprising vastus lateralis, vastus intermedius and vastus medialis, plus rectus femoris, collectively called quads. Achieving the desired effect on the leg position thus involves a very complex neurologic re-programming of at least 10 individual muscles calling for a training involving some sort of a bio-feedback tied in to the target of reducing the external torque forcing on the stifle. Provision of this feedback is the core feature of this invention.

DETAILED DESCRIPTION

Figure 1:
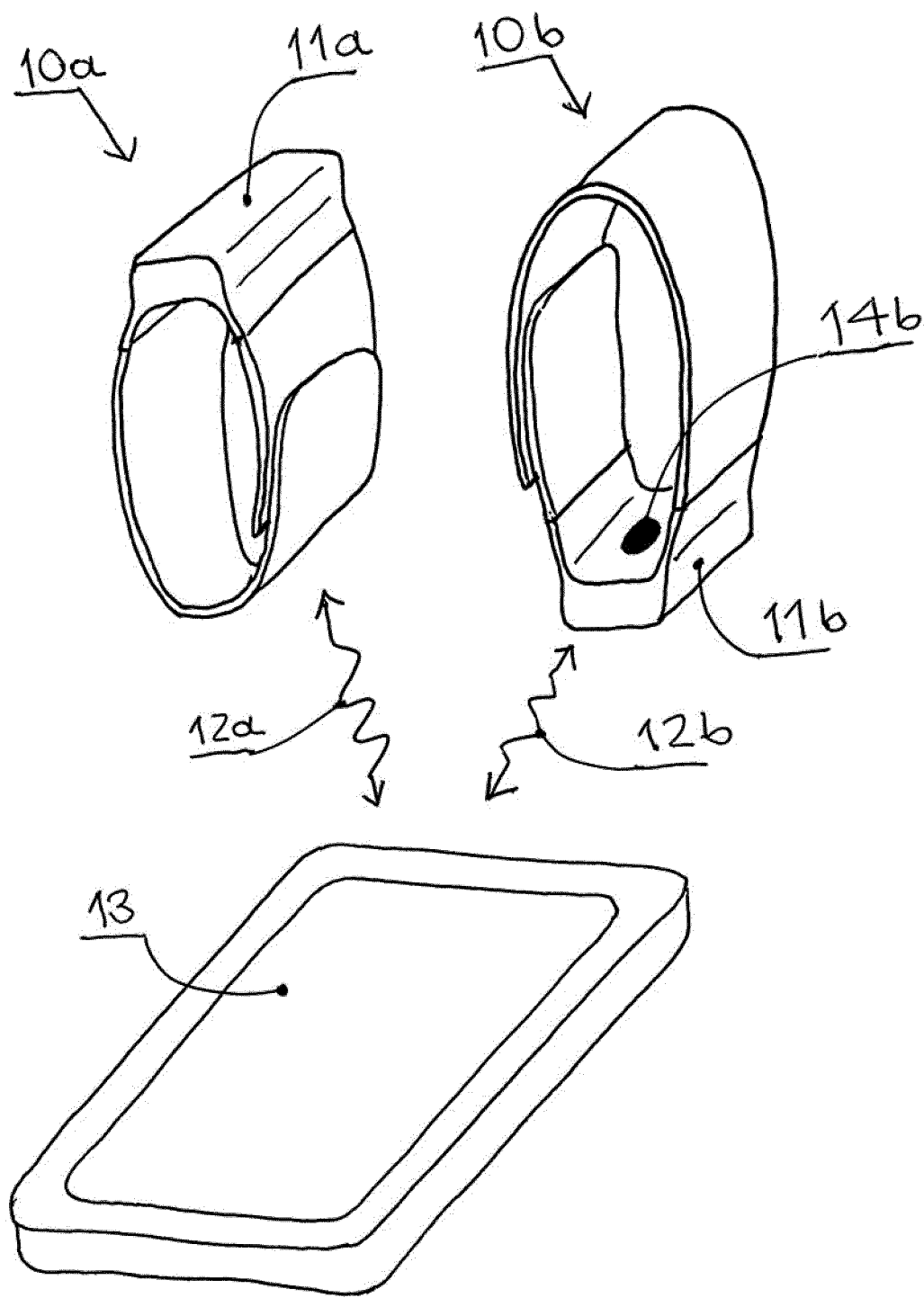
FIG. 1 is a schematic representation of the system comprising two strap-on sensors/stimulators and a controller, for example a smartphone.

The present invention provides devices and methods for the non-surgical treatment of a disordered knee in a dog, wherein the disorder may encompass a partially ruptured cranial cruciate ligament (CrCL), a fully ruptured CrCL, or a displaced patella.

A first aspect of the invention relates to a system for correcting dog gait comprising:
- at least one orientation sensor and at least one stimulator for attaching, e.g. for strapping, to a limb of the dog, e.g. two orientation sensors and stimulators for attaching to contralateral limbs, and
- a computing device receiving orientation sensor data, wherein the at least one stimulator is adapted for being activated by the computing device if the sensor data exceeds acceptable threshold levels.

In one embodiment, the device comprises at least one orientation sensor strapped to the hind limbs, preferably to the tarsal bones, communicating with the computing device, such as a smart phone, preferably via a wireless link. In some embodiments, an orientation sensor and a stimulator, e.g. an electrode, may be combined in a single device.

With the dog in locomotion, if an orientation sensors detects excessive rotations, in particular excessive internal rotation of the tibia, a weak electrical and/or mechanical stimulus is delivered as a signal to the dog by the stimulator to attempt correcting the gait—in case of cruciate ligaments at risk, the signal may be delivered to the medial aspect of the foot.

The invention has other similar applications where there are known gait patterns predisposing damage to the joints and/or ligaments, e.g. excessive front limb adduction that can lead to medial elbow disease.

The invention further relates to a non-invasive method for correcting dog gait comprising:
- attaching at least one orientation sensor and at least one stimulator to a limb of the dog, e.g. attaching two orientation sensors and stimulators to contralateral limbs of the dog,
- providing a computing device for receiving orientation sensor data, and
- activating the at least one stimulator by the computing device if the sensor data exceeds acceptable threshold levels.

In another aspect of the invention the limb placement in gait on a treadmill is controlled by a barrier. For hind limbs affected by internal tibia rotation the barrier is placed between the (hind) limbs and its width gradually increased until the intoeing is sufficiently reduced and/or eliminated.

This invention is based, at least in part, on in vitro experiments and clinical observations that have helped us identify the fundamental causes of the slow process of degradation of the CrCL in the dog. Our experimental work with dog cadavers has shown a surprisingly strong effect of the torque imposed on the stifle by the ground reaction at the paw on the tensile force in the CrCL, as well as on its surrogate, a lateral extra-capsular suture. Compared to the loading confined to the sagittal plane, where the effect of the slope is measured directly and exclusively, the tension on the CrCL and its extra-capsular surrogate was increased greatly—by up to six times—if the torsion was accounted for by applying the load to the paw. In an intact stifle, when the muscle forces fail to provide perfect balance of internal and external rotators to offset externally applied loads, the cruciate ligaments wrapping around each other provide the limit to internal rotation (Arnoczky and Marshall, *Am. J. Vet. Res.* 38(11):1807-1814, 1977). This causes very high tensile forces in the ligaments. It has been shown by observation that in nine out of ten cases of failed CrCL repair, the caudal cruciate ligament is also damaged (Sumner et al., *Veterinary Surgery*, 39:936-941, 2010). In one out of four cases in that study there was a full thickness defect of the caudal ligament. Interestingly, all geometry-modifying surgeries increase the load on the remaining caudal cruciate ligament, yet post-intervention failures are extremely rare. The explanation for this surprising observation is that in the absence of the CrCL, the tension creating wrapping of the two ligaments is gone. Periarticular tissues then take on the role of limiting the internal rotation, even if with less well-defined range and robustness.

Other than major deformities of the limb bones, which is absent in most clinical cases of CrCL, the major functional driver of torque-generating internal rotation is the popliteal muscle, which is the most highly specialized muscle acting to internally rotate the tibia (*Miller's Anatomy of the Dog*, Third Edition, W.B. Saunders Company, 1993, pg. 373). There is only sparse information available about its function in dogs, but it seems to fire mostly during the swing phase of the gait. If so, it would define the position of the paw as it lands on the ground, thus setting up pre-conditions for the torque-induced tension in the cruciate ligaments as they wrap on each other. The only plausible remedy would be perfectly timed and balanced action of the caudal portion of the biceps femoris muscle, which is the only major external rotator of the tibia. However, in the gait studies performed at the Friedrich-Schiller-University, Jena, by M. Fischer et al., the caudal portion of the biceps femoris muscle is usually not activated at the very early stance phase of the gait (see pg. 128 in *Dogs in Motion*, M. S. Fischer and K. E. Lilje, $2^{nd}$ edition 2014, VDH Service GmbH, Dortmund). Furthermore, all of the stifle spanning muscles inserting to the medial side of the proximal tibia are not only flexors, involved in controlling the stifle angle in the sagittal plane together with the quadriceps that act as stifle extensors, but also internal rotators of the tibia. The task of the caudal portion of the biceps femoris is further complicated because it also functions as a stifle flexor.

Following these intricate relationships of the muscles controlling the relative rotation at the stifle around two axes, and the extremely high tensile loads that can be developed by internal rotation of the tibia, it has been proposed in the U.S. patent application Ser. No. 15/690,611 by Tepic that the primary cause of CrCL degradation in dogs is undercompensated internal rotation of the tibia that over-stresses the cruciate ligaments.

In contrast to the surgical treatment proposed in the application Ser. No. 15/690,611, this invention advocates a preventive, non-invasive intervention aimed at training still healthy dogs to tune their muscle control mechanisms used in gait in order to avoid undesirable, high loading of the ligaments, but also of the joints, that may eventually lead to serious consequences of a chronic, gradual functional degradation.

In addition to already presented background of the hind limbs orthopedic issues, such as cranial cruciate ruptures, the same problems exist in the front limbs of the dogs, where the gait patterns leading to adduction of the front limbs create high stresses on the medial compartment of the elbow and thereafter a commonly encountered, highly debilitating elbow disease, now considered a form of dysplasia.

Hip dysplasia in dogs is perhaps the best-known condition of dysplasia that frequently leads to arthrosis of the hip. Drawing a parallel to well established problems and treatment solutions in humans, training dogs to increase abduction of their femurs in gait at very young age could prevent progression, or possibly even reverse degradation of their hip joints.

Furthermore, as suggested by the aforementioned in vitro experiments, the present invention can also be used post surgically to reduce the tension in the implants aiming to restore the function of the cranial cruciate ligament, both of intra-articular and extra-articular type.

Another very common orthopedic problem in dogs is medial luxation of the patella. A straightforward analysis by inspection suggests that this malfunction can have the same origin—external torque caused by the paw placement medially at the start of the loaded gait phase (referred to as intoeing in human gait). Due to similarities in cause, the remedy can be the same as described herein for CrCL—increasing the relative action of the external rotator (caudal portion of biceps femoris) vs. internal rotators (popliteus, sartorius, gracilis, semitendinosus, and semimembranosus). If this is done in the earlier stages of patellar luxation, no further intervention may be needed. Surgical standard of care today involves tibial tuberosity transposition and deepening of the patellar groove associated with relatively high morbidity and complications calling for revision surgeries.

As noted above, the surgical methods described herein can be applied where there is a partial rupture of the CrCL in dogs. TPLO and TTA geometry modifying procedures are currently performed for both total and partial ruptures of the ligament with about 30% of all cases being partial ruptures. Clinical signs are present and the experience suggests that most of the partial ruptures will progress to total ruptures. Performing the surgery at this earlier stage may have an important advantage in that meniscal damage is much less likely to develop until the complete rupture. Some surgeons will remove the remnants of the partially torn ligament at the time of performing TPLO or TTA, but others will leave it. There are some indications that a partially ruptured ligament will not progress to a full rupture and may even partially heal.

If the intervention according to this invention is performed in cases of partial CrCL rupture, the prospects are good that a further, much more invasive procedure, such as TPLO or TTA, will not be necessary. The cruciate ligaments may not keep wrapping on each other to limit the internal rotation of the tibia and may instead go on to heal.

As noted herein, in some situations, treatments based on this invention may be deployed alone and can alone prevent or resolve the clinical problem being addressed, while in other situations, they are performed as an adjunct intervention to improve the prospects of conventional surgeries.

Shown in FIG. 1 is a preferred embodiment of the invention comprising at least one, but preferably two devices, 10a and 10b—one to be strapped to the left and one to the right limb of the dog—provided with orientation sensors 11a and 11b. Such sensors are ubiquitous in modern electronic devices, e.g. smart phones, robots, drones, devices for gaming, augmented and virtual reality, etc. An application specific sensor node, BNO055, from Bosch Sensortec GmbH, Gerhard-Kindler-Staße 9, 72770 Reutlingen/Kusterdingen, Germany, is well suited for use in this invention. It integrates a triaxial accelerometer, a triaxial gyroscope, a triaxial geomagnetic sensor and a microcontroller, which combines all of the sensors' data into a stable three-axis orientation output. With the dog moving along with a standard gait, the orientation data from the left and the right limb, are wirelessly transmitted, 12a and 12b, to a computing device, e.g. a smartphone 13, which uses an algorithm to calculate deviations from what is considered a safe pattern of orientations. If the deviation is larger than a threshold, a stimulating electrical device, preferably contained in the same package with the sensor, delivers a small electrical signal to the deviating limb via a stimulator, e.g. an electrode 14b (or 14a, not shown). Alternatively, the stimulator can be electro-mechanical. Using bilateral sensors allows the algorithm to establish the main axis of forward gait after a several steps—orientations are then referenced to this axis and the gravity.

Figure 2:
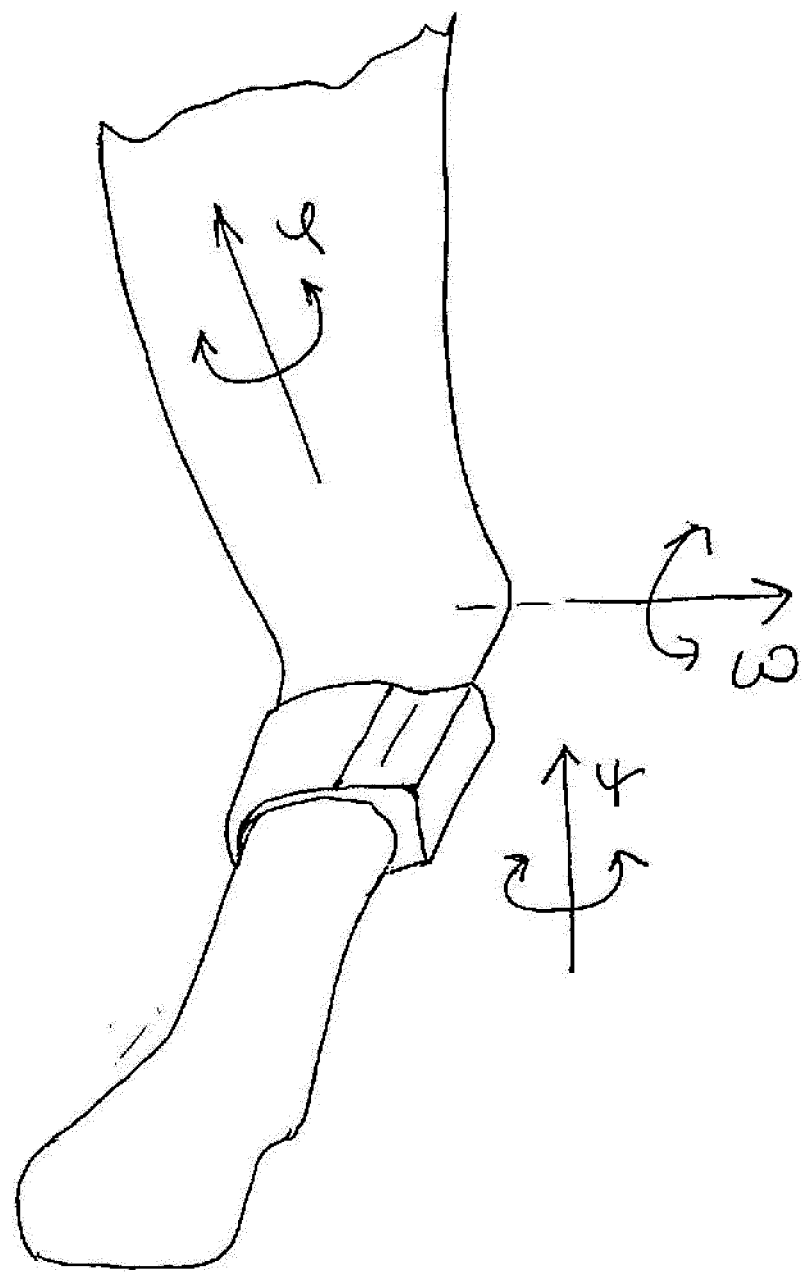
FIG. 2 shows a sensor/stimulator strapped on the tarsus of a right hind limb.

In one embodiment of the invention, the sensors/stimulators are strapped to the tarsal bones of the dog, just distally to the ankle joints, FIG. 2. There is very little tissue covering the bones in this area so that the orientations of the foot can be well approximated by measuring the orientations of the strapped-on sensor. Since the ankle joint is almost a perfect hinge with the axis of rotation, $\omega$, the sensor data on rotation, $\psi$, around the vertical can also be used to approximate the internal rotation of the tibia, $\varphi$. As presented above, excessive internal rotation of the tibia is the prime risk for cranial cruciate rupture. When the threshold of normal internal rotation is exceeded an electric signal is delivered to the medial aspect of the tarsus, just under the strap holding the sensor/stimulator to the foot. All of this sensing and stimulating is best timed to the late swing phase, before the paw lands on the ground. With sufficient time and frequency of this training process, the dog will learn how to favor the caudal portion of the biceps femoris in the balance against the internal rotators, and thus reduce the damaging internal rotation of the tibia.

This training can be best carried out by the dog owner during regular leash-walks. Walking along with the dog on a straight path, the owner activates the circuitry via e.g. a smart phone app and leaves it on as long as the dog responds appropriately. It is relatively easy to observe intoeing of the hind limbs—if the dog learns how to avoid it and gets a small award for its performance, the training could be accomplished in weeks or even perhaps in only several days, with occasional re-training to maintain the proper gait for life.

Figure 3:
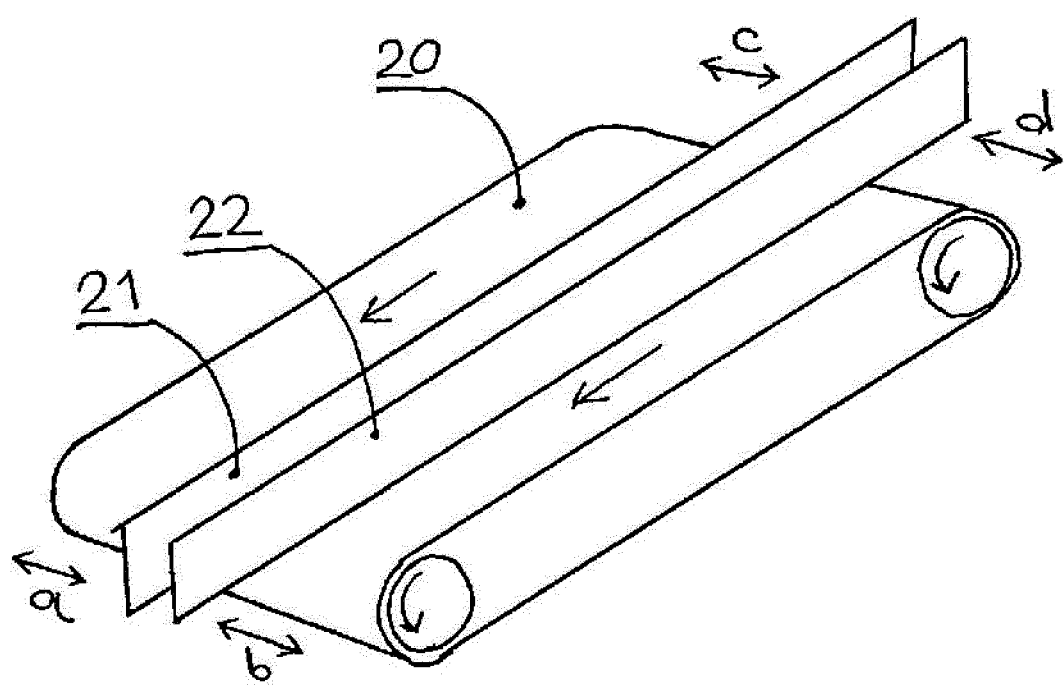
FIG. 3 shows a barrier comprising two boards spaced apart with adjustable distance to be placed between the legs of a dog on a treadmill.

In another embodiment of the invention, FIG. 3, the dog is trained to walk on a treadmill, 20, as is frequently done these days for a variety of protocols in physiotherapy. In the scope of protecting the cruciate ligaments, the goal of the training is to get the dog to avoid intoeing at the hind limbs. This can be accomplished by placing a barrier along the long axis of the treadmill, between the legs of the dog. The barrier can comprise two boards, 21 and 22, that can be gradually spread apart—as shown by arrows a, b, c and d—from each other, either in parallel, or in a wedge-shaped fashion so that the barrier is wider either between the hind limbs, when targeting tibia internal rotation to prevent cruciate disease, or between the front limbs, when targeting adduction to prevent elbow medial compartment disease. The input to the control of the gait is the width of the barrier; the feedback is the contact of the paws to the barrier, which the dog will try to avoid. The feedback could simply be mechanical contact to the barrier, or, alternatively an electrical signal—a weak electrical stimulus—when the barrier is touched.

Having disclosed at least one embodiment of the present invention, variations will be understood by one of ordinary skill in the art. Such adaptations, modifications and improvements are considered part of the invention.

The invention claimed is:
1. A system for correcting dog gait comprising:
two orientation sensors and at least one stimulator for attaching to a limb of a dog, wherein the two orientation sensors are adapted for being attached to contralateral limbs of the dog, and
a computing device receiving orientation sensor data,
wherein the at least one stimulator is adapted for being activated by the computing device when the sensor data exceeds acceptable threshold levels, wherein
the two orientation sensors are adapted for being attached to tarsal bones of the contralateral limbs, and the computing device is adapted for estimating an internal rotation of the tibiae in gait and activating the at least one stimulator adapted to deliver signals to a medial aspect of a dog's foot.

2. The system of claim 1, wherein the computing device is adapted for communicating with the two orientation sensors and the at least one stimulator wirelessly.

3. The system of claim 1, wherein the stimulator is adapted to deliver electrical signals to the dog.

4. The system of claim 1, wherein the stimulator is adapted to deliver mechanical signals to the dog.

5. The system of claim 1, wherein an orientation sensor integrates a triaxial accelerometer, a triaxial gyroscope, and a triaxial geomagnetic sensor.

6. The system of claim 1, wherein the two orientation sensors are adapted to be attached to the tarsal bones of the contralateral limbs.

7. The system of claim 6, wherein the computing device is adapted to estimate internal rotation of the tibiae in gait and activate the at least one stimulator delivering signals to the medial aspect of the foot.

8. The system of claim 1, wherein the computing device comprises a smart phone.

9. A non-invasive method for preventing cruciate rupture by correcting dog gait comprising:
attaching two orientation sensors and at least one stimulator to tarsal bones of contralateral limbs of a dog,
providing a computing device for receiving orientation sensor data, wherein the computing device estimates an internal rotation of the tibiae in gait, and
activating the at least one stimulator by the computing device when the sensor data exceeds acceptable threshold levels, wherein the at least one stimulator delivers signals to a medial aspect of the dog's foot.

* * * * *